United States Patent

Bernier et al.

Patent Number: 5,453,471
Date of Patent: Sep. 26, 1995

[54] GAS PHASE POLYMERIZATION PROCESS

[75] Inventors: Robert J. N. Bernier, Flemington; Robert L. Boysen, Lebanon, both of N.J.; Robert C. Brown, Danbury, Conn.; Leonard S. Scarola, Union; Gary H. Williams, Flemington, both of N.J.

[73] Assignee: Union Carbide Chemicals & Plastics Technology Corporation, Danbury, Conn.

[21] Appl. No.: 284,797

[22] Filed: Aug. 2, 1994

[51] Int. Cl.$^6$ .................................................. C08F 2/34
[52] U.S. Cl. .............................. 526/68; 526/88; 526/901; 526/335; 526/342; 526/347.2
[58] Field of Search .................. 526/68, 88, 901, 526/335, 342, 347.2

[56] References Cited

U.S. PATENT DOCUMENTS

| | | | |
|---|---|---|---|
| 3,254,070 | 5/1966 | Roelen | 260/94.9 |
| 3,256,263 | 6/1966 | Wisseroth et al. | 260/94.9 |
| 3,298,792 | 1/1967 | Di Drusco | 23/284 |
| 3,300,457 | 1/1967 | Schmid et al. | 260/88.2 |
| 3,652,527 | 3/1972 | Trieschmann et al. | 260/93.7 |
| 3,779,712 | 12/1973 | Calvert et al. | 23/288 E |
| 4,012,573 | 3/1977 | Trieschmann et al. | 526/68 |
| 4,379,758 | 4/1983 | Wagner et al. | 252/429 B |
| 4,383,095 | 5/1983 | Goeke et al. | 526/88 |
| 4,543,399 | 9/1985 | Jenkins, III et al. | 526/70 |
| 4,588,790 | 5/1986 | Jenkins, III et al. | 526/70 |
| 4,803,251 | 2/1989 | Goode et al. | 526/74 |
| 4,876,320 | 6/1990 | Fulks et al. | 526/62 |
| 4,933,149 | 6/1990 | Rhee et al. | 422/131 |
| 4,994,534 | 2/1991 | Rhee et al. | 526/88 |
| 5,200,477 | 4/1993 | Baker et al. | 526/74 |

*Primary Examiner*—Joseph L. Schofer
*Assistant Examiner*—Tom Weber
*Attorney, Agent, or Firm*—P. W. Leuzzi

[57] ABSTRACT

A process for producing polymers in a gas phase reactor by continuously introducing a stream of monomer and gas into a polymerization zone while maintaining the temperature within the polymerization zone below the dew point temperature of at least one monomer present in said polymerization zone.

14 Claims, 1 Drawing Sheet

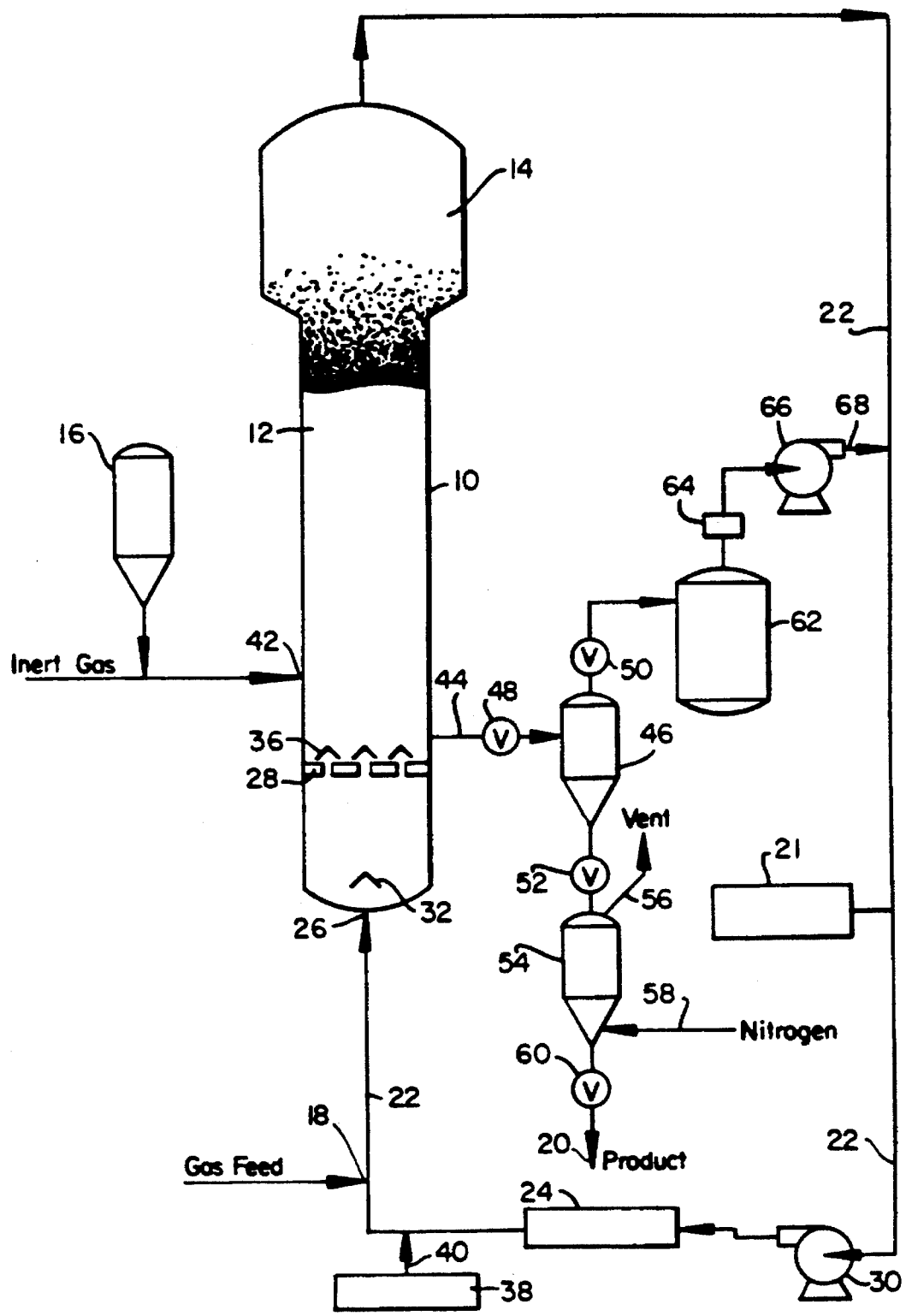

GAS PHASE POLYMERIZATION PROCESS

SUMMARY OF THE INVENTION

This invention relates to a new gas phase process capable of effecting polymerization reactions using liquid monomers in an otherwise gas-phase process.

BACKGROUND OF THE INVENTION

The discovery of gas-phase fluidized bed and stirred reactor processes for the production of polymers, especially polyolefin polymers, made it possible to produce a wide variety of new polymers with highly desirable and improved properties. These gas-phase processes, especially the gas fluidized bed process for producing such polymers provided a means for producing polymers with a drastic reduction in capital investment expense and dramatic savings in energy usage as compared to other then conventional polymerization processes.

In a conventional gas fluidized bed process a gaseous stream containing one or more monomers is passed into a fluidized bed reactor containing a bed of growing polymer particles in a polymerization zone, while continuously or intermittently introducing a polymerization catalyst into the polymerization zone. The desired polymer product is withdrawn from the polymerization zone, degassed, stabilized and packaged for shipment, all by well known techniques. Because the polymerization reaction is exothermic, substantial heat is generated in the polymerization zone which must be removed to prevent the polymer particles from overheating and fusing together. This is accomplished by continuously removing unreacted hot gases from the polymerization zone and replacing them with cooler gases. The hot gases removed from the polymerization zone are compressed, cooled in a heat exchanger, supplemented by additional amounts of monomer to replace monomer polymerized and removed from the reaction zone and then recycled into the bottom of the reactor. Cooling of the recycled gases is accomplished in one or more heat exchanger stages. The sequence of compression and cooling is a matter of design choice but it is usually preferable to provide for compression of the hot gases prior to cooling. The rate of gas flow into and through the reactor is maintained at a level such that the bed of polymer particles is maintained in a fluidized condition. The production of polymer in a stirred bed reactor is very similar, differing primarily in the use of mechanical stirring means to assist in maintaining the polymer bed in a fluidized condition.

Conventional gas phase fluidized bed resin production is very well known in the art as shown, for example, by the disclosure appearing in U.S. Pat. Nos. 4,379,758; 4,383,095 and 4,876,320, which are incorporated herein by reference.

The production of polymeric substances in gas phase stirred reactors is also well known in the art as exemplified by the process and equipment descriptions appearing in U.S. Pat. No. 3,256,263.

For many years it was erroneously believed that to allow liquid of any kind to enter into the polymerization region of a gas phase reactor would inevitably lead to agglomeration of resin particles, formation of large polymer chunks and ultimately complete reactor shut-down. This concern caused gas phase polymer producers to carefully avoid cooling the recycle gas stream entering the reactor to a temperature below the condensation temperature of any of the monomers employed in the polymerization reaction.

Comonomers such as hexene-1,4-methyl pentene and octene-1, are particularly valuable for producing ethylene copolymers-polymers. These higher alpha olefins have relatively high condensation temperatures. Due to the apprehension that liquid monomers in the polymerization zone would lead to agglomeration, chunking and ultimately shut down the reactor, production rates which depend upon the rate at which heat is removed from the polymerization zone, were severely constrained by the perceived need to maintain the temperature of the cycle gas stream entering the reactor at temperature safely above the condensation temperature of the highest boiling monomer present in the cycle gas stream.

Even in the case of polymerization reactions conducted in stirred reactors, care was exercised to maintain the resin bed temperature above the condensation temperature of the recycle gas stream components.

To maximize heat removal it was not unusual to spray or inject liquid into or onto the polymer bed where it would immediately flash into a gaseous state by exposure to the hotter recycle gas stream. A limited amount of additional cooling was achieved by this technique by the Joules-Thompson effect but without ever cooling the recycle gas stream to a level where condensation might occur. This approach typically involved the laborious and energy wasting approach of separately cooling a portion of the cycle gas stream to obtain liquid monomer for storage and subsequent separate introduction into or onto the polymerization bed. Examples of this procedure are found in U.S. Pat. Nos. 3,254,070; 3,300,457; 3,652,527 and 4,012,573.

It was discovered later, contrary to the long held belief that the presence of liquid in the cycle gas stream would lead to agglomeration and reactor shut-down, that it is indeed possible to cool the entire cycle gas stream to a temperature where condensation of significant amounts of monomer would occur without the expected dire results when these liquid were introduced into the reactor in temperature equilibrium with the recycle gas stream. Cooling the entire cycle gas stream produces a two-phase gas-liquid mixture in temperature equilibrium with each other so that the liquid contained in the gas stream does not immediately flash into vapor. Instead a substantially greater amount of cooling takes place because the total mass of both gas and liquid enters the polymerization zone at a substantially lower temperature than previously thought possible. This process led to substantial improvements in the yield of polymers produced in the gas phase, especially where comonomers which condense at relatively low temperatures are used. This procedure, commonly referred to as "condensing mode" operation, is described in detail in U.S. Pat. Nos. 4,543,399 and 4,588,790 which are incorporated by reference. In condensing mode operation the two-phase gas-liquid mixture entering the polymerization zone is heated quite rapidly and is completely vaporized within very short distance after entry into the polymerization zone. Even in the largest commercial reactors, all liquid has been vaporized and the temperature of the then totally gaseous cycle gas stream raised substantially by the exothermic nature of the polymerization reaction soon after entry into the polymerization zone. The ability to operate a gas phase reactor in condensing mode was believed possible due to the rapid heating of the two-phase gas-liquid stream entering the reactor coupled with efficient constant back mixing of the fluidized bed leaving no liquid present in the polymer bed more than a short distance above the entry level of the two-phase gas-liquid recycle stream.

We have now found that liquid monomer may be present throughout the entire polymer bed provided that the liquid monomer present in the bed is adsorbed on or absorbed in solid particulate matter present in the bed, such as the polymer being produced or fluidization aids present in the bed, so long as there is no substantial amount of free liquid monomer present more than a short distance above the point of entry into the polymerization zone, as in the case of condensing mode operation. This discovery makes it possible to produce polymers in a gas phase reactor with the use of monomers having condensation temperatures much higher than the temperatures at which conventional polyolefins are produced in gas phase reactors. This invention makes possible the gas phase production of classes of polymers which previously were thought not capable of production in a continuous gas phase process.

BRIEF DESCRIPTION OF THE DRAWING

The drawing is a schematic depiction of a fluidized bed reaction system which is particularly suited to the production of polymeric materials in accordance with the present invention.

DETAILED DESCRIPTION OF THE INVENTION

While not limited to any particular type or kind of polymerization reaction, this invention is particularly well suited to olefin polymerization reactions involving homopolymerization and copolymerization of relatively high boiling monomers.

Examples of higher boiling monomers capable of undergoing olefinic polymerization reactions are the following:
  A. higher molecular weight alpha olefins such as decene-1, dodecene-1 etc. and styrene.
  B. dienes such as hexadiene, vinyl cyclohexene, dicyclopentadiene, butadiene, isobutylene, isoprene, ethylidene norbornene and the like.
  C. polar vinyl monomers such as acrylonitrile, maleic acid esters, vinyl acetate, acrylate esters, methacrylate esters, vinyl trialkyl silanes and the like.

These higher boiling monomers can be homopolymerized in accordance with this invention with the use of an inert gas as the gaseous component of the two phase gas-liquid mixture cycled through the reactor. Suitable inert materials for this purpose include nitrogen and saturated hydrocarbons which remain gaseous at a temperature below the temperature selected to be maintained in the polymerization zone.

The higher boiling monomers can also be copolymerized with one or more lower boiling monomers such as ethylene, propylene and butene, as well as other higher boiling monomers such as those mentioned above, the only requirement being that there be a sufficient difference in the condensation temperatures of the higher boiling monomer and at least one lower boiling monomer or inert substance as will allow enough gas to be present in the cycle gas stream to permit practical, steady state, continuous operation.

In accordance with our invention the higher boiling monomers can be directly introduced into the polymerization zone or carried into the polymerization zone as with the recycle gas stream.

The practice of this invention is not limited to any particular class or kind of catalyst. Any catalyst useful in the conduct of gas phase polymerization reactions is suitable for use in the practice of this invention.

The conventional Ziegler-Natta catalysts, by which is meant those formed by reacting a metal alkyl or hydride with a transition metal salt, are preferred in the practice of this invention. Those formed by reacting an aluminum alkyl with salts of metals of groups I to III of the periodic table are particularly useful.

Illustrative of the catalysts useful in the practice of this invention are the following:
  A. Titanium based catalysts such as those described in U.S. Pat. Nos. 4,376,062; 4,379,758.
  B. Chromium based catalysts such as those described in U.S. Pat. Nos. 3,709,853; 3,709,954 and 4,077,904.
  C. Vanadium based catalysts such as vanadium oxychloride, vanadium acetyl acetonate.
  D. Metallocene catalysts such as those described in U.S. Pat. Nos. 4,530,914; 4,665,047; 4,752,597; 5,218,071, 5,272,236 and 5,278,272.
  E. Cationic forms of metal halides, such as aluminum trihalides.

DETAILED DESCRIPTION OF THE DRAWING

With reference to the drawing, the reactor 10 consists of a reaction zone 12 and a velocity reduction zone 14.

In general, the height to diameter ratio of the reaction zone can vary in the range of about 2.7:1 to about 4.6:1. The range, of course, can vary to larger or smaller ratios and depends upon the desired production capacity. The cross-sectional area of the velocity reduction zone 14 is typically within the range of about 2.6 to about 2.8 multiplied by the cross-sectional area of the reaction zone 12.

The reaction zone 12 includes a bed of growing polymer particles, formed polymer particles and a minor amount of catalyst particles fluidized by the continuous flow of polymerizable and modifying gaseous components in the form of make-up feed and recycle fluid through the reaction zone. To maintain a viable fluidized bed, the superficial gas velocity through the bed must exceed the minimum flow required for fluidization, and preferably is at least 0.1 ft/sec above minimum flow. Ordinarily, the superficial gas velocity does not exceed 5.0 ft/sec and usually no more than 2.5 ft/sec is sufficient.

It is essential that the bed always contain particles to prevent the formation of localized "hot spots" and to entrap and distribute catalyst throughout the reaction zone. On start up, the reactor is usually charged with a base of particulate polymer particles before gas flow is initiated. Such particles may be identical in nature to the polymer to be formed or they may be different. When different, they are withdrawn with the desired formed polymer particles as the first product. Eventually, a fluidized bed of desired polymer particles supplants the start-up bed.

A partially or totally activated precursor composition and/or catalyst used in the fluidized bed is preferably stored for service in a reservoir 16 under a blanket of a gas which is inert to the stored material, such as nitrogen or argon.

Fluidization is achieved by a high rate of fluid recycle to and through the bed, typically in the order to about 50 times the rate of feed of make-up fluid. The fluidized bed has the general appearance of a dense mass of individually moving particles as created by the percolation of gas through the bed. The pressure drop through the bed is equal to or slightly greater than the weight of the bed divided by the cross-sectional area. It is thus dependent on the geometry of the reactor.

Make-up fluid is fed to the bed at point 18. The composition of the make-up stream is determined by a gas analyzer 21. The gas analyzer determines the composition of the recycle stream and the composition of the make-up stream is adjusted accordingly to maintain an essentially steady state gaseous composition within the reaction zone.

The gas analyzer is a conventional gas analyzer which operates in a conventional manner to determine the recycle stream composition to facilitate maintaining the ratios of feed stream components. Such equipment is commerically available from a wide variety of sources. The gas analyzer 21 is typically positioned to receive gas from a sampling point located between the velocity reduction zone 14 and heat exchanger 24.

The higher boiling monomers can be introduced into the polymerization zone in various ways including direct injection through a nozzle (not shown in the drawing) into the bed or by spraying onto the top of the bed through a nozzle (not shown) positioned above the bed, which may aid in eliminating some carryover of fines by the cycle gas stream. If the rate of consumption is relatively small, heavier momomers can be introduced into the polymerization zone simply by suspension in the cycle gas stream entering the bottom of the reactor.

To ensure complete fluidization, the recycle stream and, where desired, part of the make-up stream are returned through recycle line 22 to the reactor at point 26 below the bed. There is preferably a gas distributor plate 28 above the point of return to aid in fluidizing the bed. In passing through the bed, the recycle stream absorbs the heat of reaction generated by the polymerization reaction.

A portion of the fluidizing stream which has not reacted in the bed is removed from the polymerization zone, preferably by passing it into velocity reduction zone 14 above the bed where entrained particles can drop back into the bed.

The recycle stream is compressed in a compressor 30 and then passed through a heat exchange zone where heat is removed before it is returned to the bed. The heat exchange zone is typically a heat exchanger 24 which can be of the horizontal or vertical type. If desired, several heat exchangers can be employed to lower the temperature of the cycle gas stream in stages. It is also possible to locate the compressor downstream from the heat exchanger or at an intermediate point between several heat exchangers. After cooling, the recycle stream is returned to the reactor at its base 26 and to the fluidized bed through gas distributor plate 28. A gas deflector 32 is preferably installed at the inlet to the reactor to prevent contained polymer particles from settling out and agglomerating into a solid mass and to prevent liquid accumulation at the bottom of the reactor as well to facilitate easy transitions between processes which contain liquid in the cycle gas stream and those which do not and vice versa. Illustrative of gas deflectors suitable for this purpose is the apparatus described in U.S. Pat. No. 4,933,149.

The selected temperature of the bed is maintained at an essentially constant temperature under steady state conditions by constantly removing the heat of reaction. No noticeable temperature gradient appears to exist within the upper portion of the bed. A temperature gradient will exist in the bottom of the bed in a layer of about 6 to 12 inches, between the temperature of the inlet fluid and the temperature of the remainder of the bed.

Good gas distribution plays an important role in the operation of the reactor. The fluidized bed contains growing and formed particulate polymer particles, as well as catalyst particles. As the polymer particles are hot and possibly active, they must be prevented from settling, for if a quiescent mass is allowed to exist, any active catalyst contained therein may continue to react and cause fusion. Diffusing recycle fluid through the bed at a rate sufficient to maintain fluidization throughout the bed is, therefore, important.

Gas distribution plate 28 is a preferred means for achieving good gas distribution and may be a screen, slotted plate, perforated plate, a plate of the bubble-cap type and the like. The elements of the plate may all be stationary, or the plate may be of the mobile type disclosed in U.S. Pat. No. 3,298,792. Whatever its design, it must diffuse the recycle fluid through the particles at the base of the bed to keep the bed in a fluidized condition, and also serve to support a quiescent bed of resin particles when the reactor is not in operation.

The preferred type of gas distributor plate 28 is metal and has holes distributed across its surface. The holes are normally of a diameter of about ½ inch. The holes extend through the plate. Over each hole there is positioned a triangular angle iron identified as 36 which is mounted on plate 28. The angle irons serve to distribute the flow of fluid along the surface of the plate so as to avoid stagnant zones of solids. In addition they prevent the polymer from flowing through the holes when the bed is settled.

Any fluid inert to the catalyst and reactants can also be present in the recycle stream. An activator compound, if utilized, is preferably added to the reaction system downstream from heat exchanger 24, in which case the activator may be fed into the recycle system from dispenser 38 through line 40.

In the practice of this invention operating temperatures can extend over a range of from about −100° C. to about 150° C. with temperatures ranging from about 40° C. to about 120° C. being preferred.

The fluid-bed reactor can be operated at pressures up to about 1000 psi and preferably at a pressure of from about 100 psi to about 350 psi, for polyolefin resin production. Operation at higher pressures favors heat transfer as an increase in pressure increases the unit volume heat capacity of the gas.

The partially or totally activated precursor composition and/or catalyst (hereinafter collectively referred to as catalyst) is injected into the bed at a rate equal to its consumption at a point 42 which is above distributor plate 28. Preferably, the catalyst is injected at a point in the bed where good mixing of polymer particles occurs. Injecting the catalyst at a point above the distribution plate is an important feature for satisfactory operation of a fluidized bed polymerization reactor. Injection of the catalyst into the area below the distributor plate could cause polymerization to begin there and eventually cause plugging of the distributor plate. Injection directly into the fluidized bed aids in distributing the catalyst uniformly throughout the bed and tends to avoid the formation of localized spots of high catalyst concentration which can cause "hot spots" to form. Injection of the catalyst into the reactor above the bed can result in excessive catalyst carryover into the recycle line where polymerization can occur leading to plugging of the line and heat exchanger may eventually occur.

The catalyst can be injected into the reactor by various techniques. It is preferred, however, to continuously feed the catalyst into the reactor utilizing a catalyst feeder as disclosed; e.g., in U.S. Pat. No. 3,779,712. The catalyst is preferably fed into the reactor at a point 20 to 40 percent of the reactor diameter away from the reactor wall and at a height of about 5 to about 30 percent of the height of the bed.

A gas which is inert to the catalyst, such as nitrogen or argon, is preferably used to carry the catalyst into the bed.

The rate of polymer production in the bed depends on the rate of catalyst injection and the concentration of monomer(s) in the recycle stream. The production rate is conveniently controlled by simply adjusting the rate of catalyst injection.

Since any change in the rate of catalyst injection will change the reaction rate and thus the rate at which heat is generated in the bed. The temperature of the recycle stream entering the reactor is adjusted upwards and downwards to accommodate any change in the rate of heat generation. This ensures the maintenance of an essentially constant temperature in the bed. Complete instrumentation of both the fluidized bed and the recycle stream cooling system is, of course, useful to detect any temperature change in the bed so as to enable either the operator or a conventional automatic control system to make a suitable adjustment in the temperature of the recycle stream.

Under a given set of operating conditions, the fluidized bed is maintained at essentially a constant height by withdrawing a portion of the bed as product at the rate of formation of the particulate polymer product. Since the rate of heat generation is directly related to the rate of product formation, a measurement of the temperature rise of the fluid across the reactor (the difference between inlet fluid temperature and exit fluid temperature) is indicative of the rate of particular polymer formation at a constant fluid velocity if no vaporizable liquid is present in the inlet fluid.

On discharge of particulate polymer product from reactor 10, it is desirable and preferable to separate fluid from the product and to return the fluid to the recycle line 22. There are numerous ways known to the art to accomplish this. One preferred system is shown in the drawings. Thus, fluid and product leave reactor 10 at point 44 and enter product discharge tank 46 through valve 48, which may be a ball valve which is designed to have minimum restriction to flow when opened. Positioned above and below product discharge tank 46 are conventional valves 50, 52 with the latter being adapted to provide passage of product into product surge tank 54. Product surge tank 54 has venting means illustrated by line 56 and gas entry means illustrated by line 58. Also positioned at the base of product surge tank 54, is a discharge valve 60 which when in the open position discharges product for conveying to storage. Valve 50 when in the open position releases fluid to surge tank 62. Fluid from surge tank 62 is directed through a filter absorber 64 and thence through a compressor 66 and into recycle line 22 through line 68.

In a typical mode of operation, valve 48 is open and valves 50, 52 are in a closed position. Product and fluid enter product discharge tank 46. Valve 48 closes and the product is allowed to settle in product discharge tank 46. Valve 50 is then opened permitting fluid to flow from product discharge tank 46 to surge tank 62 from which it is continually compressed back into recycle line 22. Valve 50 is then closed and valve 52 is opened and any product in product discharge tank 46 flows into product surge tank 54. Valve 52 is then closed. The product is purged with inert gas, preferably nitrogen, which enters product surge tank 54 through line 58 and is vented through line 56. Product is then discharged from product surge tank 54 through valve 60 and conveyed through line 20 to storage.

The particular timing sequence of the valves is accomplished by the use of conventional programmable controllers which are well known in the art. Moreover, the valves can be kept substantially free of agglomerated particles by directing a stream of gas periodically through the valves and back to the reactor.

Another preferred product discharge system which may be alternatively employed is that disclosed and claimed in the copending U.S. patent application,of Robert G. Aronson filed Jul. 28, 1981, Ser. No. 287,815, now abandoned, and entitled Fluidized Bed Discharge System. Such a system employs at least one (parallel) pair of tanks comprising a settling tank and a transfer tank arranged in series and having the separated gas phase returned from the top of the settling tank to a point in the reactor near the top of the fluidized bed. Such alternative preferred product discharge system obviates the need fro a recompression line 64, 66, 68, as shown in the system of the drawing.

The fluidized-bed reactor is equipped with an adequate venting system (not shown) to allow venting the bed during start up and shut down. The reactor does not require the use of stirring and/or wall scraping. The recycle line 22 and the elements therein (compressor 30, heat exchanger 24) should be smooth surfaced and devoid of unnecessary obstructions so as not to impede the flow of recycle fluid or entrained particles.

Illustrative of the polymers which can be produced in accordance with the invention are the following:

Polyisoprene (cis-1,4-Polyisoprene)

Polystyrene

Polybutadiene

SBR (polymer of butadiene copolymerized with sytrene)

ABS (polymer of acrylonitrile, butadiene and styrene)

Nitrile (polymer of butadiene copolymerized with acrylonitrile)

Butyl (polymer of isobutylene copolymerized with isoprene)

EPR (polymer of ethylene copolymerized with propylene)

EPDM (polymer of ethylene copolymerized with propylene and a diene such as hexadiene, dicyclopentadiene, or ethylidene norbornene)

Neoprene (polychloroprene)

Silicone (polydimethyl siloxane)

Copolymer of ethylene and vinyltrimethoxy silane

Copolymer of ethylene and one or more of acryonitrile, maleic acid esters, vinyl acetate, acrylic and methacrylic acid esters and the like.

When it is desired to produce polymers or copolymers using one or more monomers which are all relatively high boiling and which are liquids under the temperature and pressure conditions which are preferred for gas phase fluidized bed production in accordance with the invention, it is necessary to employ an inert substance which will remain gaseous under the conditions selected for polymerization in the fluidized bed. Suitable for this purpose are inert gases such as nitrogen, argon, neon, krypton and the like. Also useful are saturated hydrocarbons such as ethane, propane, butane and the like as well as halogen substituted alkanes such as freon. Other materials which remain gaseous under the desired conditions, such as carbon dioxide, provided they are essentially inert and do not affect catalyst performance, can also be employed.

Nitrogen, because of its physical properties and relatively low cost is a preferred medium for the manufacture of polymers from higher boiling mononers such as styrene, vinyl acetic acid, acrylonitrile, methylacrylate, methylmethacrylate and the like. Alkanes such as ethane and propane which remain gaseous at relatively low temperatures are also preferred.

Conventional techniques for the prevention of fouling of the reactor and polymer agglomeration can be used in the practice of our invention. Illustrative of these techniques are the introduction of finely divided particulate matter to prevent agglomeration, as described in U.S. Pat. Nos. 4,994,534 and 5,200,477; addition of negative charge generating chemicals to balance positive voltages or by addition of positive charge generating chemicals to neutralize negative voltage potentials as described in U.S. Pat. No. 4,803,251. Antistat substances may also be added, either continuously or intermittently to prevent or neutralize static charge generation.

The following examples are provided to illustrate our invention.

Example 1

In an example of the process of the invention a fluidized bed reaction system as described above, was operated as described below to produce ethylene-propylene diene terpolymer. The polymer was produced under the following reaction conditions: 40° C. reactor temperature and 290 psia reactor pressure. The partial pressures (dew points) of the monomers and comonomers inside the reactor were 90 psia for ethylene and 198 psia for propylene. The partial pressure of hydrogen was 2.0 psia. The monomer ethylidene-norbornene (ENB) was injected into the polymerization zone of the reactor at the rate of 0.53 lb/h. The volume of the reactor was 55 ft$^3$; the resin's weight inside the reactor was 112 lbs. The catalyst system employed in this Example was vanadium acetyl acetonate with diethylaluminum chloride as cocatalyst and ethyl trichloroacetate as the promoter. The production rate was 20 lb/h. The product had a Mooney value of 55.

75 percent of the injected ENB was incorporated into polymers by polymerization. The unreacted remainder of ENB, dissolved into polymers and was equal to 0.66 percent of the polymer's weight. With 112 lbs. of resins inside the reactor, the total unreacted ENB was 0.74 lbs. If the unreacted ENB were completely evaporated inside the reactor, its partial pressure would be 0.6764 psia.

At 40° C. the saturation pressure is 2187.7 psia for ethylene, 337.1 psia for propylene and 0.262 psia for ENB. Since the partial pressures of ethylene and propylene inside the reactor were much less than their saturation pressures, there was no condensed ethylene or propylene. The calculated partial pressure of unreacted ENB inside the reactor, however, is much higher than its saturation pressure. Therefore, the ENB must have remained in a liquid state and been absorbed by the polymers.

Example 2

Ethylene-propylene diene terpolymer was made in a fluidized bed reaction system as described above under the following reaction conditions: 40° C. reactor temperature and 363.4 psia. reactor pressure. The partial pressures of the monomers and comonomers inside the reactor were 90 psia. for ethylene and 198.2 psia. for propylene. The partial pressure of hydrogen was 2.2 psia., and the partial pressure of nitrogen was 72.6. The monomer ethylidenenorbornene (ENB) was injected into the polymerization zone of the reactor at the rate of 0.53 lb/h. The volume of the reactor was 55 ft$^3$; the resin's weight inside the reactor was 112 lbs. The catalyst system employed in this Example was vanadium acetyl acetonate with diethylaluminum chloride as cocatalyst and ethyl trichloroacetate as the promoter. The production rate was 20 lb/h. The product had a Mooney value of 55.

75 percent of the injected ENB was incorporated into polymers by polymerization. The unreacted remainder of ENB, dissolved into polymers and was equal to 0.66 percent of the polymer's weight. With 112 lbs. of resins inside the reactor, the total unreacted ENB was 0.74 lbs. If the unreacted ENB completely evaporated inside the reactor, its partial pressure would be 0.6764 psia.

At 40° C. the saturation pressure is 2187.7 psia. for ethylene, 337.1 psia. for propylene and 0.262 psia, for ENB. Since the partial pressures of ethylene and propylene inside the reactor were much less than their saturation pressures, there was no condensed ethylene or propylene. The calculated partial pressure of unreacted ENB inside the reactor, however, is much higher than its saturation pressure. Therefore, the ENB must have remained in a liquid state and been absorbed by the polymers.

Examples 3–6

The following examples set forth in tabular form, operating conditions for producing a variety of different polymers in accordance with the invention. They illustrate the practice of the invention using different catalyst systems and differing cycle gas compositions.

| EXAMPLE NO. | 3 | 4 | 5 | 6 |
| PRODUCT: | POLYBUTADIENE | SBR | ABS | POLYSTYRENE |
| --- | --- | --- | --- | --- |
| Reaction Conditions: | | | | |
| Temperature (°C.) | 40 | 40 | 40 | 40 |
| Pressure (psi) | 100 | 110 | 200 | 100 |
| Superficial Velocity (ft/s) | 1.75 | 2.0 | 1.5 | 1.5 |
| Production Rate (lb/h) | 30 | 25 | 20 | 40 |
| Total Reactor Volume (ft$^3$) | 55 | 55 | 55 | 55 |
| Reaction Zone Volume (ft$^3$) | 7.5 | 7.5 | 7.5 | 7.5 |
| Bed Height (ft) | 7.0 | 7.0 | 7.0 | 7.0 |
| Bed Diameter (ft) | 1.17 | 1.17 | 1.17 | 1.17 |

-continued

| EXAMPLE NO. | 3 | 4 | 5 | 6 |
|---|---|---|---|---|
| PRODUCT: | POLYBUTADIENE | SBR | ABS | POLYSTYRENE |
| Bed Weight (lbs) | 112 | 112 | 112 | 112 |
| Cycle Gas Composition: | | | | |
| $N_2$ | 20 | 27.3 | 58.0 | 99.7 |
| Butadiene | 80 | 72.5 | 39.9 | — |
| Styrene | — | .2 | 0.15 | 0.3 |
| Acrylonitrile | — | — | 1.95 | — |
| Catalyst: | Co(acac)$_3$* | Co(acac)$_3$* | Co(acac)$_3$* | Cp$_2$ZrMe$_2$** |
| Co-catalyst: | Triethylaluminum | Triethylaluminum | Triethylaluminum | MAO*** |
| Heavy Monomer Feed Rate (lb/h) | | | | |
| Butadiene | 46.2 | 9.62 | 2.46 | — |
| Styrene | — | 20.83 | 15.33 | 44.4 |
| Acrylonitrile | — | — | 7.08 | — |
| Polymer Composition: | | | | |
| Butadiene | 100 | 25 | 8 | — |
| Styrene | — | 75 | 69 | 100 |
| Acrylonitrile | — | — | 23 | — |

*Cobalttriacetylacetonate
**Dicyclopentadienylzirconiumdimethyl
***Methylalumoxane

We claim:

1. A process for producing polymers in a stirred bed or gas fluidized bed reaction vessel having a polymerization zone containing a bed of growing polymer particles which comprises:

1) continuously introducing a stream comprised of one or more monomers and optionally one or more inert gases or liquids into said polymerization zone;

2) continuously or intermittently introducing a polymerization catalyst into said polymerization zone;

3) continuously or intermittently withdrawing polymer product from said polymerization zone;

4) continuously withdrawing unreacted gases from said polymerization zone, compressing and cooling said gases while maintaining the temperature within said polymerization zone below the dew point of at least one monomer present in said polymerization zone;

with the proviso that if there is only one monomer present in said gas-liquid stream there is also present at least one inert gas.

2. A process for producing polymers from two or more monomers by an exothermic polymerization reaction in a stirred bed or gas fluidized bed reaction vessel having a polymerization zone containing a bed of growing polymer particles, which comprises:

1) continuously introducing a fluid stream comprised at least two monomers and optionally one or more inert gases or liquids;

2) continuously or intermittently introducing a polymerization catalyst into said polymerization zone;

3) continuously or intermittently withdrawing polymer product from said polymerization zone;

4) continuously withdrawing unreacted gases from said polymerization zone, compressing and cooling said gases; and 5) maintaining the temperature within said polymerization zone below the dew point of at least one of said monomers.

3. A process according to claim 1 wherein the velocity of said fluid stream entering said polymerization zone, the rate of introduction of said polymerization catalyst into said polymerization zone and the concentration of monomer in said fluid stream are such that the temperature within said polymerization zone is maintained below the dew point of at least one monomer present in said fluid stream.

4. A process according to claim 1 wherein the temperature within said polymerization zone and the velocity of gases passing through the said polymerization zone are such that essentially no liquid is present in the said polymerization zone that is not absorbed on or absorbed in solid particulate matter.

5. A process for producing polymers from two or more monomers by an exothermic polymerization reaction in a stirred bed or gas fluidized bed reactor having a polymerization zone containing a bed of growing polymer particles which comprises:

1) continuously introducing a fluid stream containing at least two monomers and optionally one or more inert gases into said polymerization zone;

2) continuously or intermittently introducing a polymerization catalyst into said polymerization zone;

3) continuously or intermittently withdrawing polymer product from said polymerization zone;

4) continuously withdrawing unreacted gases from said polymerization zone, compressing and cooling said gases; and 5) maintaining the temperature within said polymerization zone below the dew point of at least one of said monomers and above the vaporization temperature of at least one of said monomers.

6. In a continuous fluidized bed polymerization process for the production of polymer from two or more fluid monomers by passing a gaseous stream through a fluidized bed reactor in the presence of catalyst under reactive conditions, withdrawing polymeric product and unreacted fluids, cooling said unreacted fluids and returning said cooled fluids into said reactor together with sufficient additional monomers to replace those monomers polymerized and withdrawn as product, the improvement which comprises;

controlling the concentration of monomers in the gas stream passing through said reactor; the temperature of the cooled fluids returned to said reactor and the amount of catalyst present in said reactor so that the temperature within said reactor is maintained below the dew point of at least one of said monomers and above the vaporization level of at least one of said monomers.

7. A process according to claim 1 wherein said polymerization process is conducted in the presence of inert particulate matter.

8. A process according to claim 1 wherein said process is conducted in the presence of an agent or device for controlling the level of static in said reactor.

9. A process according to claim 1 wherein the static voltage in said reactor is maintained essentially neutral.

10. A process for producing polymers in a stirred bed or gas fluidized bed reactor vessel having a polymerization zone containing a bed of growing polymer particles which comprises;

1) continuously introducing a fluid stream comprised of one or more monomers and one or more inert gases into said polymerization zone;

2) continuously or intermittently introducing a polymerization catalyst into said polymerization zone;

3) continuously or intermittently withdrawing polymer product from said polymerization zone;

4) continuously withdrawing unreacted gases from said polymerization zone, compressing and cooling said gases while maintaining the temperature within said polymerization zone below the dew point temperature of at least one of said inert gases.

11. A process according to claim 10 wherein said fluid stream is a two-phase gas-liquid stream comprised of an inert gas and one or more liquid monomers.

12. A process according to claim 11 wherein said inert gas is nitrogen and said liquid monomer is butadiene or chloroprene.

13. A process according to claim 11 wherein said inert gas is nitrogen and said liquid monomer is styrene.

14. A process according to claim 11 wherein said inert gas is nitrogen and said liquid monomer is a mixture of butadiene, styrene and acrylonitrile.

* * * * *

REEXAMINATION CERTIFICATE (3727th)

United States Patent [19]
Bernier et al.

[11] B1 5,453,471
[45] Certificate Issued Feb. 9, 1999

[54] GAS PHASE POLYMERIZATION PROCESS

[75] Inventors: Robert J. N. Bernier, Flemington; Robert L. Boysen, Lebanon, both of N.J.; Robert C. Brown, Danbury, Conn.; Leonard S. Scarola, Union; Gary H. Williams, Flemington, both of N.J.

[73] Assignee: Union Carbide Chemicals & Plastics Technology Corporation, Danbury, Conn.

Reexamination Request:
No. 90/004,813, Oct. 24, 1997

Reexamination Certificate for:
Patent No.: 5,453,471
Issued: Sep. 26, 1995
Appl. No.: 284,797
Filed: Aug. 2, 1994

[51] Int. Cl.⁶ .................................................. C08F 2/34
[52] U.S. Cl. .................. 526/68; 526/88; 526/335; 526/342; 526/347.2; 526/901
[58] Field of Search ........................................ 526/901

[56] References Cited

U.S. PATENT DOCUMENTS

| | | | |
|---|---|---|---|
| 3,770,710 | 11/1973 | Futamura et al. | 526/73 |
| 4,803,251 | 2/1989 | Goode et al. | 526/59 |
| 4,994,534 | 2/1991 | Rhee et al. | 526/88 |
| 5,194,526 | 3/1993 | Hussein et al. | 526/74 |

FOREIGN PATENT DOCUMENTS

| | | |
|---|---|---|
| 595291 | 8/1987 | Australia . |
| 0 241 947 | 3/1983 | European Pat. Off. . |
| 0 110 086 | 10/1983 | European Pat. Off. . |
| 0 352 022 | 7/1989 | European Pat. Off. . |
| 0 532 582 A1 0 | 9/1992 | European Pat. Off. . |
| 0 552 946 A1 | 1/1993 | European Pat. Off. . |
| 2 019 487 | 7/1970 | France . |
| 1 288 230 | 9/1969 | United Kingdom . |

*Primary Examiner*—Fred M. Teskin

[57] ABSTRACT

A process for producing polymers in a gas phase reactor by continuously introducing a stream of monomer and gas into a polymerization zone while maintaining the temperature within the polymerization zone below the dew point temperature of at least one monomer present in said polymerization zone.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

* * * * *